United States Patent [19]

Narayanan et al.

[11] Patent Number: 5,283,228

[45] Date of Patent: Feb. 1, 1994

[54] LEACHING INHIBITION OF CROP TREATING CHEMICALS WITH AMINO CONTAINING POLYMERS

[75] Inventors: Kolazi S. Narayanan, Palisades Park; Ratan K. Chaudhuri, Butler, both of N.J.

[73] Assignee: ISP Investments, Inc., Wilmington, Del.

[21] Appl. No.: 919,317

[22] Filed: Jul. 27, 1992

[51] Int. Cl.$^5$ .............................................. A01N 25/24
[52] U.S. Cl. ...................................... 504/113; 424/407
[58] Field of Search ........................ 504/113; 424/407; A01N 25/24

[56] References Cited

U.S. PATENT DOCUMENTS 4,935,447  6/1990  Philips et al. ................... 71/DIG. 1

OTHER PUBLICATIONS

Bayer, D. E. "Effect of Surfactants on Leaching of Substituted Urea Herbicides in Soil". *Weeds* 15:249–252. 1967.

McCormick et al. "Controlled Activity Polymers with Labile Bonds to Pendant Metribuzin". in Baker, *Controlled Release of Bioactive Materials* 1980.

Dunigan et al. "Atrazine-Soil Organic Matter Interactions". *Weed Science* 19:279–282. 1971.

DelliColli, H. T. "Pine Kraft Lignin as a Pesticide Delivery System." Ch. 12 of CRC Press. *Controlled Release Technologies* 1980.

*Primary Examiner*—Glennon H. Hollrah
*Assistant Examiner*—S. Mark Clardy

*Attorney, Agent, or Firm*—Marilyn J. Maue; Joshua J. Ward

[57] ABSTRACT

This invention relates to inhibiting leaching of crop treating chemicals into the ground water, aqua-system and surrounding soil of the treatment site by contacting the plant or plant site with an effective leach inhibiting, plant tolerating amount of a protein or carbohydrate derived polymer containing pendant hydroxy and secondary, tertiary or quaternized amino groups defined by the formula $$\text{carbohydrate or protein polymer} \left[ -\text{O}(\text{CHCH}_2\text{O})_a - \text{CH}_2\overset{\text{OH}}{\underset{}{\text{CH}}} - \text{CH}_2 - \text{Y} \right] \quad A$$
$$\phantom{\text{carbohydrate or protein polymer}} \phantom{xx} R$$

wherein Y is 
$$N\begin{matrix}R_1\\ \\R_2\end{matrix} \;,\; \overset{+}{N}\begin{matrix}R_1\\-R_3X^-\\R_2\end{matrix}\;,\; -NH(CH_2)_bN\begin{matrix}R_1\\ \\R_2\end{matrix} \;\text{or}$$

$$NH(CH_2)_b\overset{+}{N}\begin{matrix}R_1\\-R_3X^-,\\R_2\end{matrix}$$

R is hydrogen or methyl;

$R_1$, $R_2$ and $R_3$ are each selected from the group of hydrogen and $C_1$ to $C_{20}$ alkyl, with the proviso that, in the above formula A, at least one of $R_1$ and $R_2$ or at least one of $R_1$, $R_2$ and $R_3$ is other than hydrogen;

$X^-$ is an anion; a has a value of from 0 to 20 and b has a value of from 2 to 18.

11 Claims, No Drawings

LEACHING INHIBITION OF CROP TREATING CHEMICALS WITH AMINO CONTAINING POLYMERS

In one aspect, this invention relates to a polymeric material which is readily incorporated into an agrichemical formulation in order to inhibit leaching of the active agrichemical into the ground water and surrounding area of treatment. In another aspect the invention relates to a composition for more effective use and reduced amounts of an active agrichemical.

BACKGROUND OF THE INVENTION

Agrichemical contamination is a growing concern since more than 12 different pesticides have been found in the ground water in at least 25 states in this country alone. Studies have shown that pesticide residues in ground water are increasing and are particularly severe where agronomic and horticultural crops are grown in permeable sandy soils or in locations which receive heavy rainfall. Among the chemicals which are particularly troublesome are herbicides such as bromacil, atrazine, metribuzin, dicamba and metolachlor, nematicides such as aldicarb, fungicides such as triforine, penconazole and insecticides such as bendiocarb, diazinone, chloropyrophos and ethion, which have been found in drinking water. Hence, there is an acute need to restrict the downward movement of pesticides, herbicides and other organic pollutants in the soil without reducing their agricultural efficacy.

Control of agrichemical leaching is a complex art which depends on many factors including rainfall, soil acidity and type, as well as plant tolerance. Various solutions to the problem have been proposed including controlled release formulations and encapsulated suspensions of the harmful active chemical. Surfactants have been employed for restricting the downward movement of urea herbicides such as diuron, linuron and monuron (see Weeds, by D. E. Bayer, Vol. 15, pages 249-252, 1967). The mobility of metribuzin in the soil has been reduced by the use of polyvinyl alcohol polymers, as discussed by C. L. McCormick and M. M. Fooladi, (1980) (Controlled Activity Polymers with Labile Bonds to Pendent Metribuzin in Controlled Release of Bioactive Materials, R. Baker, Academic Press, New York, pages 317-330). However, it was found that metribuzin formed covalent linkages with the polyvinyl alcohols which resulted in hindering its release from the alcoholic polymer for plant uptake. Certain pine craft lignins have shown some decrease in the leaching losses of atrazine and 2,4-D (see Weed Science, E. P. Dunigan and T. Macintosh, 1971, Volume 19 pages 279-282 and Controlled Release Technologies: Methods, Theory and Application by H. T. Dellicolli, 1980, Volume II, C.R.C. Press, Boca Raton, Fla., pages 225-234). Several other leaching inhibitors have been proposed; however, the chemicals currently used to inhibit downward movement have been found to be highly specific to certain chemical types and do not extend generally to plant treating agrichemicals of different chemical classes.

Accordingly, it is an object of this invention to provide a leach inhibiting chemical which is more broadly effective in preventing or inhibiting downward movement of various plant treating materials.

Another object of this invention is to provide an economically produced chemical which prevents or minimizes the movement of toxic chemicals in the soil and retains the plant treating agent in the root or immediate surrounding area of the soil where it is applied and where it is most effective.

Another object of this invention is to provide a leach inhibiting chemical composition which permits more efficient use of a crop treating agent in reduced amounts and which prevents or minimizes contamination of the aquasystem.

These and other objects of the invention will become apparent to one skilled in the art from the following description and disclosure.

THE INVENTION

For effective leaching control, a balance between hydrophilic and hydrophobic moieties in the control agent is required. This balance depends upon the structure and properties of the active component, i.e. the agrichemical and the components in its formulation with conventional additives such as surfactants, carriers, emulsifiers, etc. This balance is achieved by means of the present leach controlling agent which is incorporated into the agrichemical formulation by blending, by complexing or by coprecipitating with the active agrichemical. Another important aspect of leaching control in the present invention is the presence of a soil anchoring group which is satisfied by the pendant tertiary, secondary or quaternized amino groups in the present copolymer. These cationic moieties depending from the carbohydrate polymer backbone are exposed and readily accessible to the negatively charged silicate-containing surface of the soil. Thus, in accordance with this invention, there is provided a leach inhibiting, nitrogen-containing carbohydrate polymer having pendant secondary, tertiary or quaternized amino groups which is readily formulated or incorporated with a plant treating agent to hinder or prevent migration of the plant treating agent into the ground water, aqua-system or soil areas vicinal to the treating site.

The present polymers are preferably derivatives of naturally occurring plant and animal polycarbohydrates and proteins, such as a hydrolyzed animal protein, e.g. keratin, a linear polycarbohydrate such as a polysacharide, e.g. starch, cellulose, guar gum or partially hydrolyzed polycarbohydrates of the above. Other suitable polymers include the alkoxylated derivatives of vinyl alcohol polymer or vinyl alcohol/vinyl acetate copolymer. The present leach inhibiting polymers of this invention are derivatized by the following general equation.

$$\text{polymer-OH} + C_2\text{-}C_3 \text{ alkylene oxide} + \underset{R_2}{\overset{R_1}{N R_3}} + C_3 \text{ epoxy halide}$$
(optional)

$$\text{polymer} -\text{O}-(\text{CHCH}_2\text{O})_a-\text{CH}_2-\underset{\text{R}}{\overset{\text{OH}}{\text{CH}}}-\text{CH}_2-\text{Y}$$

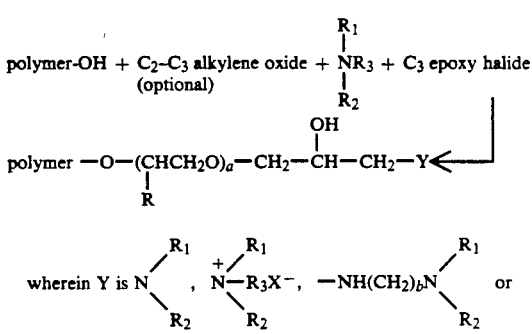

wherein Y is $N\begin{smallmatrix}R_1\\R_2\end{smallmatrix}$ , $\overset{+}{N}\begin{smallmatrix}R_1\\-R_3X^-\\R_2\end{smallmatrix}$ , $-NH(CH_2)_bN\begin{smallmatrix}R_1\\R_2\end{smallmatrix}$ or -continued

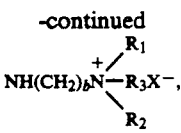

R is hydrogen or methyl $R_1$, $R_2$ and $R_3$ are each selected from the group of hydrogen and $C_1$ to $C_{20}$ alkyl, with the proviso that, in the above formula, at least one of $R_1$ and $R_2$ or at least one of $R_1$, $R_2$ and $R_3$ is other than hydrogen;

$X^{31}$ is an anion; a has a value of from 0 to 20 and b has a value of from 2 to 18.

The carbohydrate polymers of this invention include steardimonium hydroxyethyl cellulose (e.g. CRODA-CEL QS), laurdimonium hydroxyethyl cellulose (CRODACEL QL) cocadimonium hydroxyethyl cellulose (CRODACEL QM); guar hydroxypropyl triammonium chloride; a polymeric quaternary ammonium salt of hydroxyethyl cellulose with a trimethyl ammonium hydroxypropylated epoxide (POLYQUATERNIUM-10 or UCARE POLYMER 400); quaternized alkyl polyvinyl alcohol/acetate copolymer (ARLATONE PQ 225); guar gum polymerized 2-hydroxy-3-(trimethyl ammonium) propyl ether chloride (HICARE 1000) and the like.

The present polymers are those having a number average molecular weight of between about 50,000 and about 1,000,000, preferably between about 60,000 and about 150,000. Those polymers having a polydispersity of from about 2 to about 8, most desirably between about 3 and 4, are considered the best for providing uniform formulations of high efficiency.

The above polymer/agrichemical composition is applied to the plant or surrounding soil area in a pre-emergent or post-emergent application and in an effective leach inhibiting, plant tolerating amount. In formulation with the active agrichemical, as little as 0.001 weight % of instant polymers, based on the total composition, is effective to inhibit leaching of various agrichemicals. However, a weight ratio of agrichemical to polymer of between about 0.1:1 and about 10:1 is recommended and between about 0.3:1 and about 2:1 is preferred. The resulting agrichemical/leach inhibitor composition is formulated to provide a liquid, preferable of a sprayable consistency, and in some cases may require the addition of an inert diluent.

Representative crop treating agents which are commonly employed and which are controlled by the present leach inhibition agents include a wide range of herbicides, nematocides, insecticides, fungicides and other crop treating products. These include herbicides such as Dicamba, Alachlor, Aldicarb, Amiben, Arsenal, Assert, Atrazine, Bentazon, Bromacil, Bialaphos, Butylate, Carbofuran, Chloramben, Chlortoluron, Cyanazine, Banval, Cotoran, Dalapon, 2,4-D, Dicamba, Dinoseb, Diquat, Diuron, EDB, EPTC, Glyphosate, Glean, (Chlorosulfuron) Hyvar, Linuron, Lexone, Lontrel, Monuron, Metribuzin, Mecoprop, Nortron, Norflurazon, Pramitol, Prometryn, Pyramin, Rhizobitoxin, Reflex, (fomesafen) Scepter, (imazaquin) Simazine, Sinbar, Tordon, Tentoxin, Terbacl, Trifluraline, Ureas, Velpar, etc.; insecticides such as Azodrin, Diazinon, Dylox, Furadan, Metasystox, Mocap, Phosphamidon, Temik, Trigard, Vydate; nematocides such as Aldicarb; fungicides such as Triforine, Pemonazole, Bendiocerb and others cited in The Agricultural Handbook, 2nd Ed., Royal Society of Chemistry, 1987. The agrichemicals which are particularly compatible and efficacious with the present leach inhibiting agents include atrazine, dicamba, bromoil, diuron, assert bisulfate, simazine, diazinone, perconazide, triforine and metolachlor.

All of the above agrichemicals are known and appropriate plant dosages and tolerances have been described for each product. Also their agrichemical formulations are well known and such are compatable with the present leach inhibiting agents in the aforementioned concentrations. The formulated active agents can be sprayed or misted to contact treating sites according to known procedures.

The inhibiting effect of the present polymers is achieved by their complexing, encapsulation, or blending with the agrichemical and applying to a plant site. In the leach inhibiting copolymers of the present invention, the amino group provides the hydrophilic moiety and the alkyl chain of the polymer provides the hydrophobic portion. Correct balance between the hydrophilic and hydrophobic portions enable bonding of the agrichemical to the polymer and also cause a portion of the polymer to bind to the soil surface by either hydrophobic or hydrophilic interaction with organic matter in the soil. Thus, the polymer, together with the agrichemical, is more securely bound to the soil site where it is applied and leaching by rain water is significantly reduced. In all instances, using the above active chemicals, a marked reduction, and in some cases, almost complete elimination of downward transmigration of the agrichemical from the immediate application area through the soil stratum is achieved.

The agrichemical formulations containing the present polymers can be directly prepared by simply mixing the polymer into the standard agrichemical formulation or a preformed agrichemical concentrate thereof followed by recommended dilutions under ambient conditions. With certain agrichemicals, complexing with the polymer provides the highest leaching inhibition, with others, blending with the polymer achieves best results. The soil also has an important role in leaching such that the greatest leachability is found in highly porous, low organic Florida soils; whereas the loamy or clay soils of the midwest or northeast suffer least.

An advantage of the present leach inhibiting compounds is that they are non-specialized with respect to a certain group of agrichemical treating agents since the molecule contains both lipophilic and hydrophilic moieties. Also, the use of the present compounds affords more efficient use of the agrichemical since the later is retained in the immediate surrounding soil area or in the vicinity of the plant root system. Thus, somewhat smaller amounts of the agrichemical are often efficacious. Additionally the present polymers provide control of agrichemical leaching over a prolonged period of time so that less agrichemical need be applied in the next crop application. Another advantage is that the present polymers of lower molecular weight do not alter the dispersion properties of the agrichemical formulation and in some cases may enhance sprayability. In those cases where incorporation of the polymer results in raising the viscosity to an undesirable level, an inert diluent such as a petroleum distillate, mineral oil, water, ethylene glycol, etc. can be added to the formulation. Various surfactants can also be included in the agrichemical formulation. These include anionic sulfonates, e.g. lignin sulfonate, naphthalene/formaldehyde condensate sulfonate, etc. and non-ionic alkoxylated phenols, e.g. ethoxylated or propoxylated nonyl or octyl phenols which can be present in an amount up to about 15 wt. % of the total composition.

Another advantage of the present invention is that the leach inhibiting formulation can also be applied as a powder for crop dusting; in which case the formulation is dried to a particulate solid before use. A further advantage of the present polymers is that they are non-toxic and environmentally safe; thus, they do not add to soil contamination. Additionally, the presence of amine-containing polymers adds to the organic content of the soil, thus benefiting future crops. These and many other advantages will be realized by the use of the present polymeric compounds.

Having thus generally described the invention, reference is now had to the accompanying examples which illustrate specific and preferred embodiments, but which are not to be construed as limiting to the scope of the invention as more broadly described above and in the appended claims.

EXAMPLES I–XII

Blends of the above polymer/agrichemicals in commercial formulations containing surfactant, emulsifier and diluent were prepared as follows.

The polymer (5.0 g on 100% basis) was added to each of the following commercial agrichemical liquid formulations A–C to provide a weight ratio of 1:1 polymer to agrichemical and diluted with water to obtain a solution containing 10 wt. % of polymer and 10 wt. % of agrichemical.

A. Banvel herbicide containing 40% Dicamba in 4 lbs/gal of water
B. Aatrex 4L containing 40.8% Atrazine
C. Dual containing 86.4% Metolachlor to provide a 28.6% solution for A, a 29.0% solution for B and a 46.4% solution for C.

The polymers tested were
1. CRODACEL QS
2. CRODACEL QM
3. HICARE 1000
4. ARLATONE PQ 225

The indicated polymer/agrichemical formulation was introduced into a 130 cm×10 cm soil packed column. In these experiments, 2.5 cm simulated rainfall was used for Dicamba 7.5 cm simulated rainfall for Atrazine and Metolachlor was employed by adding water at the rate of 1.5 cm/hr. After leaching, the columns were allowed to drain overnight and split longitudinally into two halves. Each half was planted with alfalfa or rye grass (as indicated) in 5 cm spaced rows. The % injury as a function of herbicide movement at different heights are shown in the following Table I.

At every 15 cm from bottom of the column, a ridge of silicone was applied on the inside wall of each half of the column to prevent "ledge flow" of water along the soil-wall interface. A PVC end-cap with a small drain hole was fitted to the bottom of the column and the columns were packed with Florida soil from respective depths to provide a Florida soil profile. Soil-packed columns were kept in upright position and the soil was saturated with water and allowed to drain overnight; after which the commercial formulation of herbicide (5 kg ai/ha) with or without polymers (5 kg/ha) was introduced to the top of the column. A 2 ml solution of each treatment was applied uniformly on the soil surface as several drops using pasteur pipet. Columns were leached by pouring distilled water over filter paper placed on the soil surface to ensure uniform distribution of water and leaching was measured at 15, 30, 45, 60 and 60+ cm depths.

TABLE I

| | | Rye Grass Injury (Application rate 10 kg/ha or 8.9 lbs/acre) Column Depth (cm) | | | | | | Total % |
|---|---|---|---|---|---|---|---|---|
| Example | Polymer | Agrichemical | 0–15 | 15–30 | 30–45 | 45–60 | 60–120 | Decrease |
| I | 1 | C | 100 | 89 | 70 | 5 | 0 | 21 |
| II | 2 | C | 100 | 94 | 60 | 19 | 0 | 18 |
| III | 3 | C | 100 | 100 | 80 | 18 | 0 | 11 |
| IV | 4 | C | 100 | 90 | 80 | 10 | 0 | 16 |
| Control V | — | C | 100 | 100 | 84 | 50 | 0 | 0 (Control) |

| | | Alfalfa Injury (Application rate 5 kg/ha or 4.5 lbs/acre) Column Depth (cm) | | | | | | | Total % |
|---|---|---|---|---|---|---|---|---|---|
| Example | Polymer | Agrichemical | 0–15 | 15–30 | 30–45 | 45–60 | 60–75 | 75–90 | 90–120 | Decrease |
| VI | 1 | B | 100 | 83 | 31 | 25 | 0 | 0 | 0 | 20 |
| VII | 2 | B | 100 | 95 | 43 | 2 | 0 | 0 | 0 | 23 |
| VIII | 3 | B | 100 | 80 | 11 | 0 | 0 | 0 | 0 | 43 |
| IX | 4 | B | 100 | 75 | 20 | 10 | 0 | 0 | 0 | 35 |
| X Control | — | B | 100 | 100 | 81 | 34 | 0 | 0 | 0 | 0 Control |
| XI | 1 | A | 100 | 100 | 100 | 100 | 79 | 12 | 0 | 6 |
| XII Control | — | A | 100 | 100 | 100 | 100 | 91 | 34 | 0 | 0 Control |

The above examples illustrate various embodiments and preferred leach inhibiting compositions of this invention; however, it will be understood that substitutions of the crop treating chemicals referred to in the foregoing description, or their mixtures, can be made to replace those used in the respective Examples without departing from the scope of this invention. Similarly, any of the polymers set forth in the foregoing disclosure, or their mixtures, can be substituted for those employed in the above Examples, to provide leach inhibition of the agrichemical selected. From the above description, it will also become apparent that many modifications and alterations can be made in the preparations of the leach inhibiting compositions which are within the scope of this invention.

What is claimed is:

1. A leaching inhibited agrichemical composition comprising an active agrichemical and an effective leach inhibiting amount of a polymer having pendant hydroxy and amino groups and defined by the formula $$\text{polymer-O(CHCH}_2\text{O)}_a\text{—CH}_2\text{CH—CH}_2\text{—Y}$$
with pendant OH on the CH and R on the CHCH$_2$O unit wherein
the polymer moiety is selected from the group of a naturally occurring carbohydrate or hydroxylated protein polymer, a vinyl alcohol homopolymer and a vinyl alcohol/vinyl acetate copolymer;
R is hydrogen or methyl;

Y is $-N(R_1)(R_2)$, $-N^+(R_1)(R_2)R_3 X^-$, $-NH(CH_2)_b N(R_1)(R_2)$ or
$-NH(CH_2)_b N^+(R_1)(R_2) R_3 X^-$, where
$R_1$, $R_2$ and $R_3$ are each selected from the group of hydrogen and $C_1$ to $C_{20}$ alkyl, with the proviso that at least one of $R_1$ and $R_2$ or at least one of $R_1$, $R_2$ and $R_3$ is other than hydrogen;
$X^-$ is an anion;
a has a value of from 0 to 20; and
b has a value of from 2 to 18.

2. The composition of claim 1 wherein said polymer moiety is a polycarbohydrate.

3. The composition of claim 2 wherein said polymer moiety is a quaternized alkyl polyvinyl alcohol/acetate copolymer.

4. The composition of claim 1 wherein said polymer moiety is guar gum.

5. The composition of claim 1 wherein said agrichemical is a herbicide.

6. The composition of claim 1 wherein a is zero.

7. The composition of claim 1 wherein a has a positive value.

8. The composition of claim 1 which comprises a standard agrichemical formulation to which at least 0.001 wt. % of said polymer based on the formulation has been added.

9. The composition of claim 1 wherein the weight ratio of agrichemical to said polymer is between about 0.1:1 and about 10:1.

10. The composition of claim 8 wherein the weight ratio of agrichemical to said polymer is between about 0.3:1 and about 2:1.

11. The process of applying to a plant or plant site an effective leach inhibited amount of the composition of any one of claims 1, 2, 3, 4 or 5.

* * * * *